United States Patent
Ahmed et al.

(10) Patent No.: US 12,337,095 B2
(45) Date of Patent: Jun. 24, 2025

(54) PRESSURE MEASUREMENT IN THE EXTRACORPOREAL BLOOD CIRCUIT

(71) Applicant: B. Braun Avitum AG, Melsungen (DE)

(72) Inventors: Fakher Ahmed, Pfungstadt (DE); Silvie Krause, Melsungen (DE); Henrik Wolff, Melsungen-Adelshausen (DE); Tobias Wuerschmidt, Hann Muenden (DE)

(73) Assignee: B. Braun Avitum AG, Melsungen (DE)

( * ) Notice: Subject to any disclaimer, the term of this patent is extended or adjusted under 35 U.S.C. 154(b) by 654 days.

(21) Appl. No.: 17/611,537

(22) PCT Filed: May 20, 2020

(86) PCT No.: PCT/EP2020/064175
§ 371 (c)(1),
(2) Date: Nov. 15, 2021

(87) PCT Pub. No.: WO2020/234407
PCT Pub. Date: Nov. 26, 2020

(65) Prior Publication Data
US 2022/0211929 A1 Jul. 7, 2022

(30) Foreign Application Priority Data
May 21, 2019 (DE) .................... 10 2019 113 561.3

(51) Int. Cl.
*A61M 1/36* (2006.01)
*A61M 1/16* (2006.01)
(Continued)

(52) U.S. Cl.
CPC ........ *A61M 1/3639* (2013.01); *A61M 1/1605* (2014.02); *G01L 9/0001* (2013.01); *G01L 27/002* (2013.01); *A61M 2205/3331* (2013.01)

(58) Field of Classification Search
CPC .............. A61M 1/3639; A61M 1/1605; A61M 2205/3331; A61M 1/1621; G01L 9/0001; G01L 27/002
(Continued)

(56) References Cited

U.S. PATENT DOCUMENTS

| | | | |
|---|---|---|---|
| 6,503,062 B1 | 1/2003 | Gray et al. | |
| 6,857,318 B1 * | 2/2005 | Silber | ........................ G01L 7/02 73/730 |

(Continued)

FOREIGN PATENT DOCUMENTS

| | | |
|---|---|---|
| CN | 101858811 A | 10/2010 |
| CN | 104069557 A | 10/2014 |

(Continued)

OTHER PUBLICATIONS

Search Report received in German Application No. 10 2019 113 561.3 dated Mar. 3, 2020, with translation, 14 pages.
(Continued)

*Primary Examiner* — Marrit Eyassu
(74) *Attorney, Agent, or Firm* — Christopher A. Rothe; CM Law

(57) ABSTRACT

A device and method for calibrating a first pressure sensor. The method includes: a) recursive analysis and forecasting of at least one correction function for finding a correction signal for the correction of a drift signal with the aid of a corresponding pressure reference signal, which is measured by the first pressure reference sensor, at constant internal pressure and at constant internal tube temperature; b) first calibration of a force signal, measured by the first pressure sensor and corrected using the correction signal, with the pressure reference signal, which is measured by the first pressure reference sensor, prior to an active use of the tube; and c) second calibration of the force signal, measured by (Continued)

the first pressure sensor and corrected using the correction signal, with the pressure reference signal, which is measured by a second pressure reference sensor during an active use of the tube.

10 Claims, 8 Drawing Sheets

(51) Int. Cl.
*G01L 9/00* (2006.01)
*G01L 27/00* (2006.01)
(58) Field of Classification Search
USPC .......................................................... 73/1.57
See application file for complete search history.

(56) References Cited

U.S. PATENT DOCUMENTS

| | | | |
|---|---|---|---|
| 7,993,297 | B2 | 8/2011 | Vinci et al. |
| 9,233,199 | B2 | 1/2016 | Krause et al. |
| 9,649,421 | B2 | 5/2017 | Klewinghaus |
| 9,903,779 | B2 | 2/2018 | Hammerschmidt |
| 9,951,766 | B2 | 4/2018 | Akita et al. |
| 10,732,063 | B2 | 8/2020 | Szasz et al. |
| 2003/0217602 | A1 | 11/2003 | Steger |
| 2010/0139407 | A1 | 6/2010 | Dannhauer et al. |
| 2010/0275673 | A1 | 11/2010 | Kouda et al. |
| 2013/0158896 | A1* | 6/2013 | Schintee ............... G01L 1/04 702/41 |
| 2015/0238677 | A1 | 8/2015 | Akita et al. |

FOREIGN PATENT DOCUMENTS

| | | | | |
|---|---|---|---|---|
| CN | 105555331 | A | 5/2016 | |
| CN | 105865702 | A | 8/2016 | |
| DE | 19747254 | A1 * | 5/1999 | ........ A61M 5/16854 |
| DE | 19747254 | C2 | 1/2000 | |
| DE | 19918714 | A1 | 11/2000 | |
| DE | 102015109450 | A1 | 12/2016 | |
| EP | 1357372 | A1 | 10/2003 | |
| EP | 2725335 | A1 | 4/2014 | |
| IT | TO20011222 | A1 | 6/2003 | |
| JP | 201483092 | A | 5/2014 | |
| KR | 20180094190 | A | 8/2018 | |
| WO | 2018210931 | A1 | 11/2018 | |
| WO | 2018230400 | A1 | 12/2018 | |

OTHER PUBLICATIONS

Search Report received in International Application No. PCT/EP2020/064175 dated Aug. 27, 2020, with translation, 6 pages.
Office Action received in Japanese Application No. 2021-569369 dated May 28, 2024, with translation, 14 pages.
Written Opinion received in International Application No. PCT/EP2020/064175 dated Aug. 27, 2020, with translation, 16 pages.
Office Action received in Japanese Application No. 2021-569369 dated Nov. 8, 2024, with translation, 15 pages.
Office Action received in Chinese Application No. 202080044630.2 dated Sep. 30, 2024, with translation, 12 pages.

* cited by examiner

PRESSURE MEASUREMENT IN THE EXTRACORPOREAL BLOOD CIRCUIT

CROSS-REFERENCE TO RELATED APPLICATIONS

This application is the United States national phase entry of International Application No. PCT/EP2020/064175, filed May 20, 2020, and claims priority to German Application No. 10 2019 113 561.3, filed May 21, 2019. The contents of International Application No. PCT/EP2020/064175 and German Application No. 10 2019 113 561.3 are incorporated by reference herein in their entireties.

FIELD

The present disclosure relates to a method as well as to a device for calibrating a pressure measurement or force sensor measurement values for determining an internal tube pressure in the extracorporeal circuit for correcting the measurement value determined by the pressure measurement with a correction signal when using force sensors directly applied/adjacent/abut to a filled tube.

BACKGROUND

In general, it is possible to measure an internal tube pressure with the aid of a pressure measuring line. The (first) tube, whose internal pressure is to be measured, is connected to a pressure measurement line (second tube), which in turn feeds the pressure to be measured to a (piezoelectric) pressure sensor/pressure transducer. For this purpose, the pressure measuring line is connected to the (first) tube via a T-piece. The pressure sensor is arranged at the upper (free) end of the pressure measurement line, preferably with a Luer lock connection. Between a liquid column in the pressure measuring line and the pressure transducer, there is an air cushion which changes (expands or shrinks) when the pressure in the (first) tube changes, which in turn leads to a corresponding deflection of the pressure transducer.

Such a pressure measuring method or measuring system has, among other things, the disadvantages that in the event that, for example, blood in connection with an extracorporeal circuit or another air-oxidizing liquid flows through the (first) tube, a fluid-air contact occurs within the pressure measuring line, the manufacturing and assembly costs of the tube increase due to the T-piece, and cleaning of the pressure measuring line is made more difficult by this measuring setup. In addition, there is a risk of direct contact between the pressure sensor/pressure transducer and the liquid.

In order to avoid blood-air contact, for example, which is particularly disadvantageous in applications such as dialysis, so-called 'pressure pods' are used. Here, the pressure is not transferred directly from blood to the air cushion, for example, but blood and air are separated from each other by a flexible membrane. A change in pressure inside the (first) tube deflects the membrane, and this force is transmitted via an air cushion adjacent to the membrane to a pressure sensor, which measures the internal tube pressure. This means that also in this known design, an air cushion is provided as pressure transmission medium between the membrane and the pressure sensor, although direct contact between the air cushion and the fluid flowing in the (first) tube is avoided. This measurement setup also has the disadvantage that it entails high manufacturing costs.

Therefore, for example in EP 1 357 372 A1, a clamping device is provided in which a (first) tube is clamped, the internal pressure of which is to be measured. The internal tube pressure is measured non-invasively, i.e. with the aid of a force measurement via the outer wall of the tube and not, for example, via a T-branch for connection between the tube interior and a measurement sensor system. The expansion of the tube due to an internal tube pressure change is transmitted via a force-transmission means to a force sensor, which outputs a force signal. The change in the force signal is converted proportionally into a pressure change using a proportionality factor. In the event of a pressure change, only the tube deformation at a gap extending longitudinally through a support body of the clamping device is evaluated to generate the force signal.

However, the viscoelastic behavior of the tube has to be taken into account when measuring the internal tube pressure via the clamping device. This means that when the tube is clamped, a reset force/restoring force is generated in the form of a drift signal which superimposes the force signal or pressure signal to be measured. With a longer measuring time, the reset force has the effect that the internal pressure in the (first) tube appears to drop even under constant conditions. In order to solve this problem, it has so far been assumed that the pressure signal can be corrected by referencing with ambient air. This means that the viscoelastic behavior is investigated before active use of the tube by filling the tube with air. The resulting reset signal is then subtracted from the displayed pressure course (in the tube filled with a liquid, e.g. blood) during active use. However, a tube filled with a medium/liquid behaves differently from a tube filled with air. Therefore, a pressure signal referenced with ambient air does not give an indication of the pressure signal of a filled tube (filled with fluid).

In order to be able to correct such a distorted pressure signal, the document DE 197 47 254 C2 provides a method for correcting a pressure signal which is measured via a clamping device according to the preceding description. For this purpose, the course of the reset force is represented in the form of a relaxation function, which is tube-dependent and is known (determined) in advance. The parameters of this function are determined from the measured force signal. With the aid of this relaxation function, the force signal can be corrected and the pressure signal can be determined via a linear relationship with the force signal.

SUMMARY

Against this background, it is the object of the present invention to further improve the correction of the force signal and to correct the drift signal caused by the mechanical properties of the (first) tube before and during an active use of the (first) tube (an active use of the tube means, for example, a tube connected to a patient or a tube during a therapy) using a reference signal. Furthermore, relative pressure changes as well as the absolute internal tube pressure should preferably be determined with a pressure accuracy of ±10 mmHg.

The invention therefore provides a method for calibrating a first force sensor/a first pressure sensor, which measures a first pressure, in particular an arterial pressure, for example in an extracorporeal (blood) circuit, in the form of a force signal inside a (first) tube filled with fluid, preferably a dialyzer tube. The pressure sensor abuts directly on/is directly adjacent to the (first) tube and is integrated/inserted into a first clamping device in order to correct a drift signal caused by the (first) tube by a tube parameter-independent correction function using a pressure reference signal acquired by a first (separate) pressure reference sensor. According to the invention, the following steps are performed:

a) regression analysis and prediction of at least one tube parameter-independent correction function for finding a correction signal for correcting the drift signal using a/the corresponding pressure reference signal measured by the first pressure reference sensor at a constant internal tube pressure and at a constant internal tube temperature;

b) first calibrating of the force signal, measured by the first force sensor and corrected using the correction signal, with the pressure reference signal measured by the first pressure reference sensor before active use of the tube; and c) second calibrating of the force signal measured by the first force sensor and corrected using the correction function (predicted before) with the pressure reference signal measured by a second (separate) pressure reference sensor during active use of the tube.

In other words, a method for online correction of a force-pressure signal is provided, which according to the invention is applied to a filled (first) tube before and during active use of the (first) tube. This means that at first a first calibration of a (test/simulation) force signal generated by a first force sensor is performed before active use of the (first) tube using a pressure reference signal determined using a pressure reference sensor and a tube parameter-independent correction function. Then, a second calibration of a (second) force signal already corrected using the correction function is performed during active use of the tube, based on a pressure reference signal that is/was preferably generated by a second pressure reference sensor.

In concrete terms, a mathematical correction function and a two-point calibration are applied in such a way that absolute pressure measurement is possible. The pressure measurement is carried out via a/the force sensor integrated in a/the clamping device. The mathematical correction function is determined at constant internal tube pressure and at constant internal tube temperature, preferably within a few minutes after insertion of the (first) tube into the clamping device, from the measured (text) force pressure signal and from a reference pressure, which is determined via a (separate) pressure reference sensor (which has a different setup and/or different installation than the force sensor) and supplies a drift signal. The pressure reference sensor preferably has a higher measuring accuracy than the corresponding pressure/force sensor. A/the first calibration is then performed, in which the internal tube pressure and the internal tube temperature are constant during the acquisition of the pressure/force signal for the determination of the correction function. In a subsequent recalibration (second calibration), the (first) tube is subjected to a constant, known pressure and the correction function is determined again from the pressure data measured during this period. Such a reference method thus comprises a calibration procedure both before active use of the tube and during active use of the tube, i.e. the reference method is carried out before and during (dialysis) therapy on the patient.

Such a method allows pressure measurement via a clamping device directly on the filled (first) tube as part of a tube system. With this type of pressure measurement, the Luer lock connections used in the prior art are no longer required in the area of the clamping device. This results in lower manufacturing costs for the tube system and in improved usability. The improved usability of the tube system is due to the fact that, compared to conventional systems, fewer connectors have to be connected, and thus a machine using such a tube system can be upgraded more quickly, leakages occur less frequently and the tube system is more clearly designed. Furthermore, this tube system has the advantage that tube fluid-air contact is reduced or avoided. In the case where the fluid flowing through the (first) tube is blood, the risk of blood clotting is reduced. Thus, fewer anticoagulants have to be added to the blood, which reduces treatment costs. Furthermore, there is no wear on machine-side pressure connections (Luer lock connections), and the risk of contamination due to pressure measurement is suppressed.

The main advantage of the method according to the invention, however, is that a reference measurement during active use of the (first) tube provides significantly more accurate values than a sole reference measurement before active tube use. The correction function determined in the method according to the invention can be carried out independently of the tube material or the tube dimensions and can therefore also be used universally for unknown tube systems.

The method may be configured in such a way that, in addition to the first pressure, a second pressure measured with a second force sensor/a second pressure sensor integrated in a second clamping device can be measured and corrected. Thereby, the force signal of the second force sensor is calibrated in the first calibration and in the second calibration with the pressure reference signal measured with the second pressure reference sensor. In this way, the internal tube pressures can be measured and corrected at two different points in an extracorporeal circuit without fluid-air contact.

An advantageous embodiment of the method according to the invention, provides that the (first) tube (for example an extracorporeal blood tube of a dialysis machine or of a blood pump) comprises an arterial portion (blood inlet portion) and a venous portion (blood outlet portion). The first and/or second pressure/force sensor and the first pressure reference sensor are preferably arranged at the arterial portion. The second pressure reference sensor, which may be a pressure/force sensor for checking the internal tube pressure in the venous portion, which (as the only one) does not interact with a clamping device, is arranged on the venous portion. That means that the pressure in the venous portion of the (first) tube is measured (as the only one) via the second pressure reference sensor preferably according to a conventional pressure measurement method, e.g. via a T-piece or a flexible membrane (with increased accuracy). This means that the second pressure reference sensor (as the only one) is further preferably connected via a Luer lock connection to the machine to which the (first) tube is connected. The referencing is thus carried out via a pressure reference sensor, which is more expensive than the sensor integrated in a clamping device, but has a higher accuracy. The first pressure reference sensor is arranged in the area of the arterial tube portion and preferably has a piezoelectric element for pressure measurement.

Furthermore, it may be provided that the constant internal tube pressure can be achieved by adjusting a pump ratio between a first pump, in particular a blood pump, and a second pump, in particular a dialysate input flow pump or dialysate output flow pump. It is particularly reliable and simple to generate a constant pressure in the tube by adjusting a pumping ratio between these two pumps. For the method according to the invention, a constant pressure in the filled tube is essential.

Furthermore, the method may be configured such that the drift signal is or corresponds to the reset force of the clamped tube.

Furthermore, it is conceivable that the (corrected) force signal is converted into a pressure signal using the corresponding pressure reference signal via linear recursion, or that the force signal is calibrated with the pressure reference signal. This linear recursion enables a simple calculation of the pressure signal from the respective force signal.

Another embodiment, provides that in the case of two force sensors being used, the first force sensor is arranged, in particular integrated, at an inlet opening/a blood inlet of the first pump and the second force sensor is arranged, in particular integrated, at an outlet opening/a blood outlet of the first pump. Since in this case the tube material at the position of the force sensors, the temperature in the tube, and the insertion time of the tube into the corresponding clamping devices are identical, the expected drift behavior at the positions of the two force sensors should also be identical.

Furthermore, a device is provided having an extracorporeal circuit and at least one pressure/force sensor, in particular an arterial pressure/force sensor and/or a dialysate input pressure/force sensor, integrated in a clamping device, for internal tube pressure measurement in a fluid-filled tube with arterial and venous portion. Furthermore, the device comprises at least one pressure reference sensor for referencing a pressure/force signal which is output by the at least one pressure sensor. The at least one pressure reference sensor, in particular an arterial and/or venous pressure reference sensor, is not configured as a clamping device or is not provided to be integrated in a clamping device (configuration without clamping device). Furthermore, the device preferably comprises at least a first pump and a second pump. The device is provided and adapted to use the method for calibrating the pressure signal of the at least one pressure sensor using a reference signal of the at least one pressure reference sensor according to at least one of the preceding aspects of the invention.

Finally, a calibration device is provided for calibrating the measurement of at least a first (internal) tube pressure, preferably an arterial pressure. This first pressure is measured in the form of a force signal in a fluid circuit, in particular an extracorporeal (blood) circuit inside a tube (not part of the device) filled with the fluid/liquid/blood, with the aid of a first force sensor/a first pressure sensor/force sensor of the calibration device which is in direct contact or can be brought into direct contact with the tube (on the outside). The pressure/force sensor is integrated in a first clamping device. The first pressure is calibrated to correct a drift signal caused by the (first) tube (tube material) by a tube parameter-independent correction function using a pressure reference signal acquired/generated by a first pressure reference sensor of the calibration device. The calibration device has the following units or portions:

a) a first computer section (CPU unit/program step) provided and adapted for analyzing and predicting at least one correction function for finding a correction signal for correcting the drift signal using a corresponding (force/) pressure reference signal measured/generated by the first pressure reference sensor at constant internal tube pressure and at constant internal tube temperature;

b) a second computer section (CPU unit/program step) provided and adapted for a first calibration of the force signal measured by the first pressure/force sensor (PA) and then corrected using the correction signal with the pressure reference signal measured/generated by the first pressure reference sensor, before operational use of the tube; and c) a third computer section (CPU unit/program step) provided and adapted for a second calibration of the force signal measured by the first pressure/force sensor and then corrected using the correction signal with the (force/) pressure reference signal measured/generated by a second pressure reference sensor during active (operational) use of the tube.

In the following, two embodiments of the method according to the invention are described in detail with reference to the accompanying drawings.

BRIEF DESCRIPTION OF THE DRAWING FIGURES

DETAILED DESCRIPTION

Embodiments of the present disclosure are described below based on the accompanying figures. It should be noted that the figures shown are exemplary only and are not limiting.

First Embodiment

Overall Method

Figure 1:
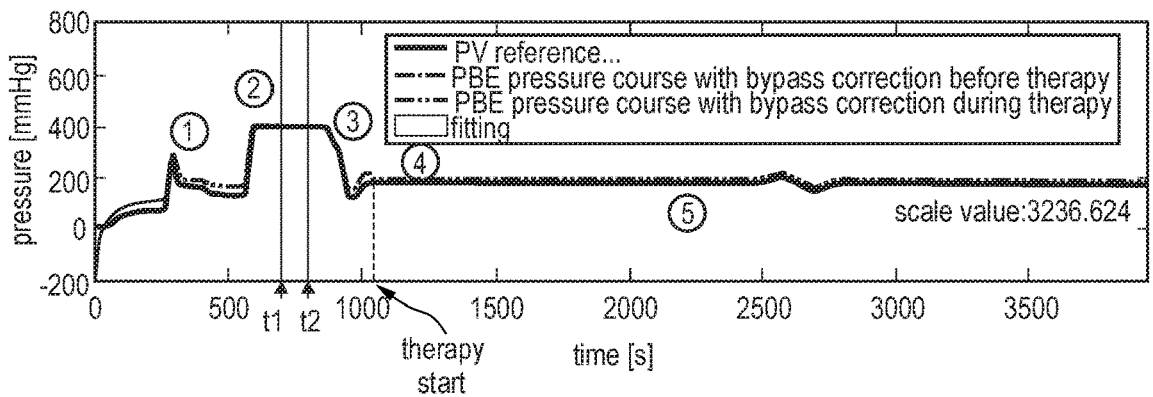
FIG. 1 shows a diagram that illustrates the pressure course in a clamping device over time by way of example.

FIG. 1 shows an example of the pressure course in millimeters of mercury (mmHg) of a pressure sensor (here the PBE pressure sensor, which is explained in more detail below) with time t in seconds (s).

In phase 1, a tube is inserted into two clamping devices, into each of which at least one pressure sensor is integrated and measures a pressure in the form of a force signal, at a dialysis machine and the tube is filled with a fluid. The tube system is filled by varying the flow pump speed of at least one pump. In this phase, leak tests are also carried out on the machine and tube.

In phase 2, the pressure in the tube is kept constant. After a short settling phase, the already described step a) is performed for regression analysis and prediction of at least one correction function for finding a correction signal for correcting the drift signal using a corresponding pressure reference signal. In step a), a correction function f is determined as a function of time t with two constants $a_0$, b for the viscoelastic behavior of the tube before therapy. The two constants $a_0$ and b are determined using a mathematical method referred to hereinafter as 'fitting'. This method is explained below. With the aid of this function, a drift signal in the form of a force signal of the respective pressure sensor is determined.

In phase 3, a pressure drop can be detected, which is used to correct the force signal using the correction function determined in step a). Furthermore, the corrected force signal of the pressure sensor is converted into a corrected pressure signal using the correspondingly provided pressure reference signal of a pressure reference sensor via a linear relationship between reference signal and corrected force signal. The pressure reference sensor is a conventional pressure sensor. Phase 3 thus shows the sequence of step b), which takes place before the start of therapy. In step b), the corrected force signal is calibrated with the pressure reference signal of the corresponding pressure reference sensor before the therapy. Calibration may also be performed using a second constant pressure level.

A conventional pressure sensor is a pressure sensor that is not integrated in a clamping device and in which no reset force influences the pressure signal. With a conventional pressure sensor, an internal tube pressure is determined, for example, via a T-piece or a pressure pod or something similar (described above).

In phase 4, after a predetermined time after the start of therapy, preferably after 5 minutes, the newly corrected force signal is calibrated again with the pressure reference signal of the corresponding pressure reference sensor. In phase 4, step c) is thus carried out.

In phase 5, the course of therapy is illustrated during which the PBE pressure is largely constant. It can be seen that the corrected PBE pressure signal and the reference signal are superimposed, which means that the correction of the pressure signal is sufficient and also works with varying pressure (see time interval between approx. 2600-2700 s).

The clamping device, which serves as a pressure sensor, the structure of a machine for which the method according to the invention is used, and steps a) to c) are described in detail and by way of example below. Furthermore, alternative embodiments of the invention are given below.

Background

Figure 2A:
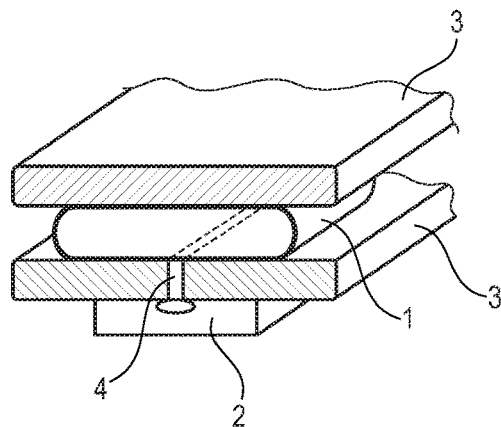
FIG. 2A shows a clamping device in which a tube is clamped.

FIG. 2A shows a (first) tube 1 whose internal pressure can be measured by a force sensor 2. For this purpose, the tube 1 is clamped in a clamping device 3. This (clamping device 3) clamps the tube 1 and an expansion or contraction of the tube 1 is transmitted to the force sensor 2 via a force-transmission means 4. The change in force that the force sensor 2 can measure is proportional to the change in internal pressure in the tube 1.

Figure 2B:
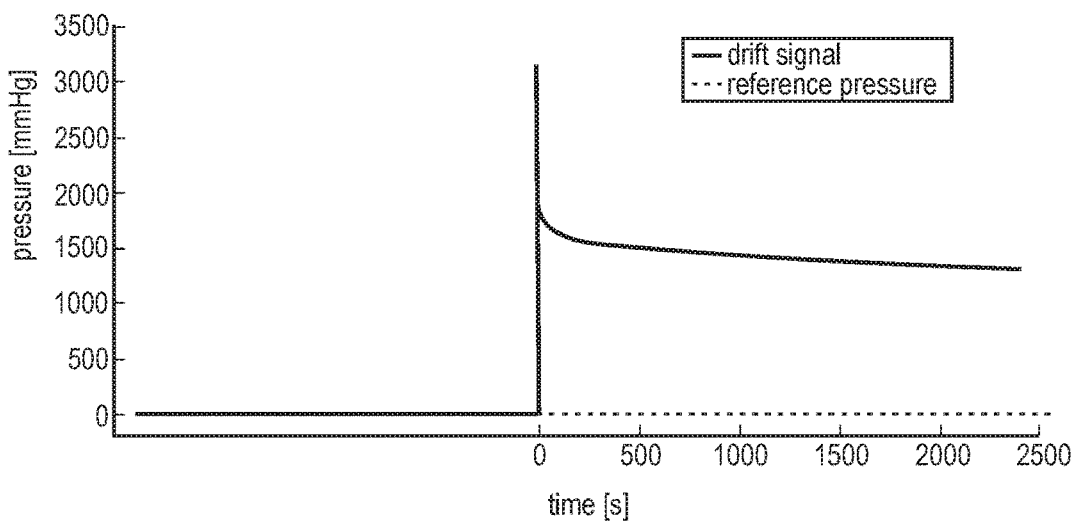
FIG. 2B shows a diagram showing the course of a drift signal compared to a reference signal.

FIG. 2B shows a graph which displays the pressure course of a drift signal and the pressure course of a reference signal over time. The pressure signal/drift signal shown is the course of a pressure in the tube 1 clamped into the clamping device 3 at time t0. The reference pressure has a value of 0 mmHg (ambient pressure) over the entire time curve shown. The pressure signal shows a pressure increase at time t0 and then a logarithmically decreasing pressure course, which can be explained by the reset force of the tube. This drift signal has to be subtracted from the actual measurement signal, so that the absolute pressure equals the reference pressure.

Set-Up for Carrying Out the Method According to the Invention

Figure 3A:
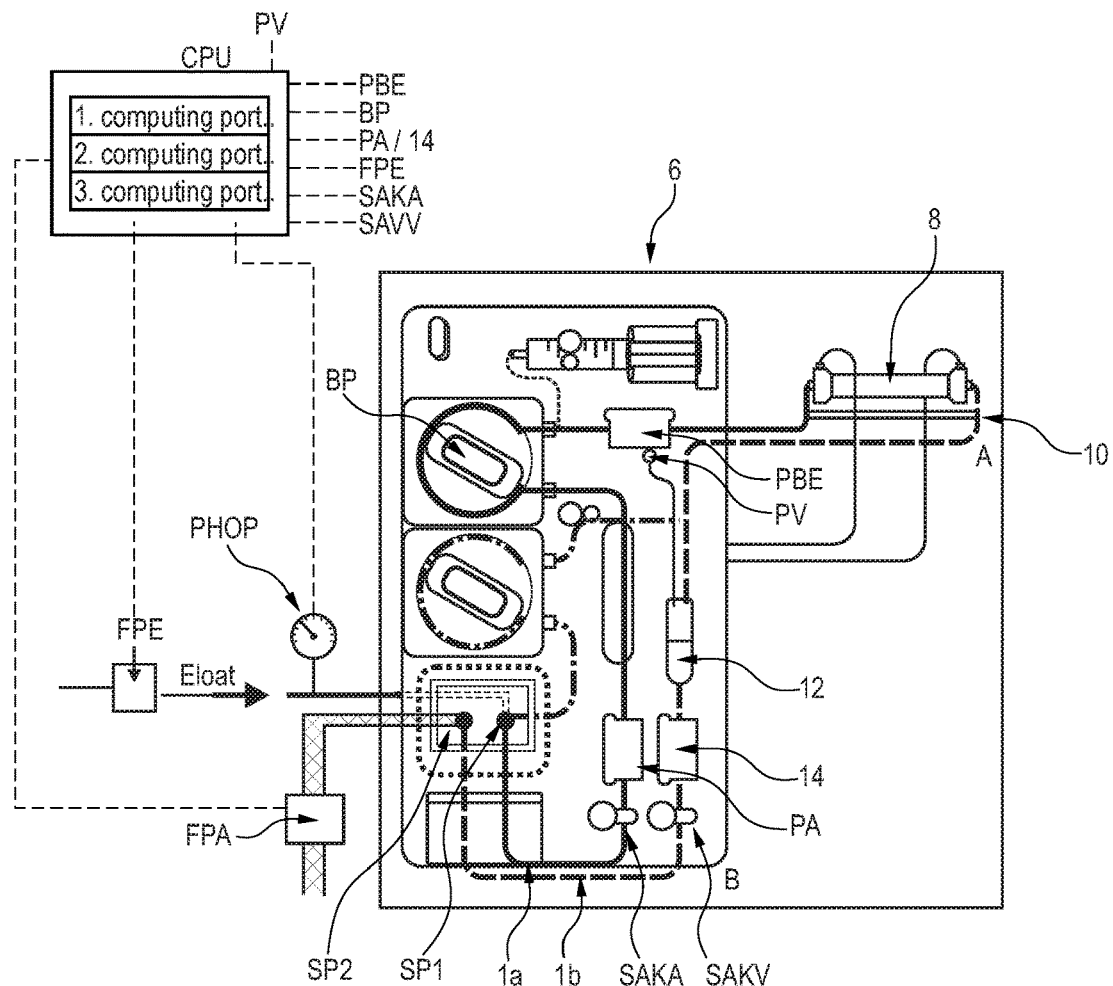
FIG. 3A shows the front of a dialysis machine in a state before active use of the tube.

FIG. 3A shows the front of a dialysis machine 6, to which a (first) tube 1 is attached, the internal pressure of which is to be measured at various points. The dialysis machine 6 has an extracorporeal circuit. The tube 1 has an arterial portion/branch 1a and a venous portion 1b. A first substituate port SP1 connects the arterial portion 1a of the tube 1 to the machine 6, and a second substituate port SP2 connects the venous portion 1b of the tube 1 to the machine 6. In the embodiment shown, the tube 1 is not connected to a patient, that is, the tube is not in active use and therefore in a state before therapy. Therefore, the tube 1 is not filled with blood but with another fluid, which is a substitute (electrolyte fluid/eloat).

The fluid is first conveyed into the arterial tube portion 1a via a dialysate input flow pump FPE, which is located outside the front of the dialysis machine 6. Before the fluid reaches the front of the dialysis machine 6, a first pressure reference sensor PHOP measures the internal tube pressure or takes a reading of the internal tube pressure. The pressure reference sensor PHOP is thus also arranged at the substituate port SP and is an additional pressure sensor compared to conventional dialysis machines 6. After the fluid enters the front of the dialysis machine 6, it first passes the arterial tube clamp SAKA, which is usually open. Then the fluid passes the first clamping device, which is also called PA pressure sensor or first pressure sensor PA, and thus the first force sensor. The first clamping device is integrated in the front side of the dialysis machine 6. The PA sensor measures the pressure in the arterial portion 1a of the tube 1. The pressure reference sensor PHOP can be used for referencing the first pressure sensor PA, since it has a higher measuring accuracy than the first pressure sensor PA.

The fluid then reaches the first pump, a blood pump BP, which continues to convey the fluid. Finally, the fluid passes a second clamping device, also called a PBE pressure sensor or second pressure sensor PBE, and thus the second force sensor. The PBE pressure sensor measures the dialysate inlet pressure at a point downstream of the blood pump BP in the flow direction of the medium in the tube. Behind the PBE pressure sensor, the fluid may pass through a dialyzer 8.

However, in the case of a bypass circuit via the bypass 10, it is also possible that the fluid does not flow through the dialyzer, but bypasses it. The venous tube portion 1b is located behind the dialyzer/bypass in the direction of fluid flow. At a point downstream of the dialyzer/bypass and upstream of an air trap/deaerator 12, where air trapped in the fluid is removed from the fluid, the fluid in the venous tube portion 1b passes a conventional pressure transducer, which is referred to as a PV measurement point. The conventional pressure transducer may be, for example, a T-piece or a pressure pod.

After the PV measuring point, the fluid passes through the deaerator 12, then through an air detector 14 and finally through a venous tube clamp SAKV, which is normally open. The venous and arterial tube clamp SAKV, SAKA are only closed in the event of a fault and block the patient access during therapy. Such an error may be, for example, that the air detector detects an amount of air greater than a certain threshold. After the fluid has passed through the venous tube clamp SAKV, it flows out via the substitute port SP2 with the aid of a pump output of a dialysate output flow pump FPA, which is arranged outside the front of the dialysis machine 6.

Furthermore, FIG. 3A shows that the dialysis machine 6 is connected to a CPU having a first computer portion, a second computer portion, and a third computer portion. Here, the CPU can control the dialysate input flow pump FPE, the dialysate output flow pump FPA, the pressure reference sensor PHOP, the pressure reference sensor PV, the first pressure sensor PA, the second pressure sensor PBE, the blood pump BP, the arterial tube clamp SAKA, and the venous tube clamp SAKV.

Figure 3B:
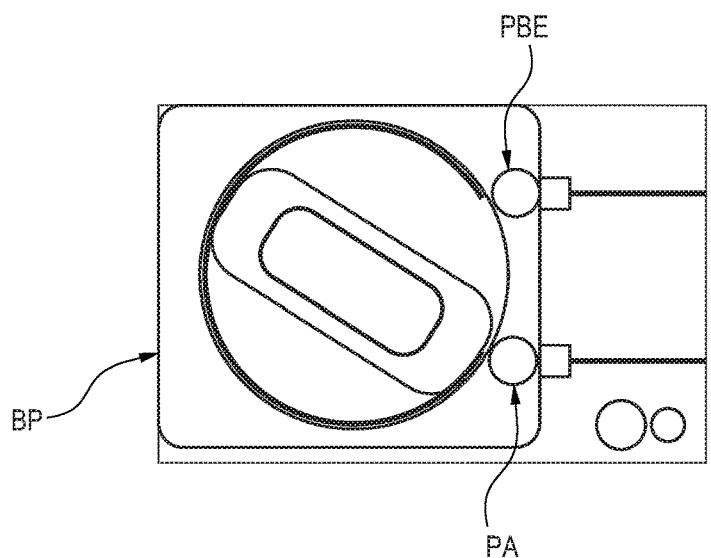
FIG. 3B shows an alternative arrangement of two sensors.

FIG. 3B shows the blood pump BP and an alternative arrangement of the first and second pressure sensors PA and PBE. In this case, the first (arterial) pressure sensor PA is located directly at the blood inlet of the blood pump BP and the second (dialyzer inlet) pressure sensor PBE is located directly at the blood outlet of the blood pump BP. In this case, both pressure sensors PA and PBE are integrated into the blood pump BP and the tube material, the temperature and the insertion time of the tube for both pressure sensors PA, PBE are identical. The expected drift behavior is also identical for both pressure sensors PA, PBE. Thus, the differential pressure $P_{PBE}-P_A$ of both pressure sensors can be determined without correction of the drift, i.e. without calibration. The differential pressure $P_{PBE}-P_A$ should correspond to the difference of the corrected pressures $P_{PBE\_korr}-P_{A\_korr}$ during the entire therapy. By comparing the two differential pressures (uncorrected with corrected difference), the correctness of the correction function, which is described later, can be assessed. If the differential pressures differ from each other by more than a predetermined amount, recalibration of the system is advisable.

Step a)

Figure 4:
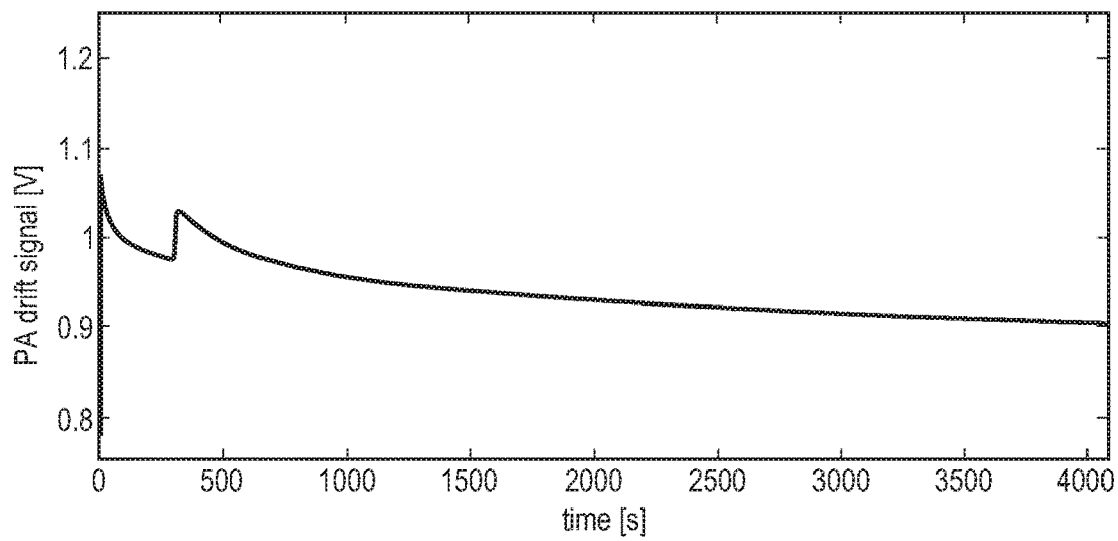
FIG. 4 shows a diagram showing the drift behavior of a tube in a closed clamping device.

Similar to FIG. 2B, FIG. 4 shows the signal course of the clamped tube after closing the clamping device. However, the force signal of the first pressure sensor PA is shown here as an example in the form of voltage values in the unit volt (V) over time t in seconds (s). At time t0 (t0=0 s), the clamping device is closed. The signal course already known from FIG. 2B is shown for a period of time before and during therapy. The decrease in the signal course can be explained by the viscoelastic properties of the tube material, which influences the pressure transmission between the force sensor and the fluid in the tube. The elastic portion of the tube generates a reset force. The viscous part of the tube leads to a slow, irreversible deformation of the tube. This tube deformation causes the reset force to decrease and thus also the force with which the tube presses against the force sensor. The reset force course shown in FIG. 4 is also referred to as a drift signal. In order to be able to represent the force signal or pressure signal of the force sensor as a signal that depends only on the internal tube pressure, it is useful to determine the drift signal in order to be able to calculate/eliminate it from the measured force signal or pressure signal, i.e. to subtract the drift signal from the measured force signal.

The viscoelastic behavior of the tube generally follows equation (1), so that the drift signal can be described as a mathematical correction function, which thus follows the following equation:

$$f(t)=a_0 \cdot t^{-b} \tag{1}$$

Here, t is the time and $a_0$ and b are unknown constants. f(t) has the unit V, since the force signal is output as a voltage value.

For further use of the equation, it is useful to determine the constants $a_0$ and b by fitting. For this purpose, it is necessary to generate a constant internal tube pressure by adjusting the pumping ratio of the pumps BP and FPE or FPA. Furthermore, a constant internal tube temperature is required. The substitute flowing through the tube is pre-heated to 36°, so that the internal tube temperature is also constant. Furthermore, the force signal of a pressure sensor, here of the first pressure sensor PA, is determined in a measurement. However, the force signal of another pressure sensor, such as the second pressure sensor PBE, can also be used. The course of the force signal of the first pressure sensor PA over time can be seen in FIG. 5.

Figure 5:
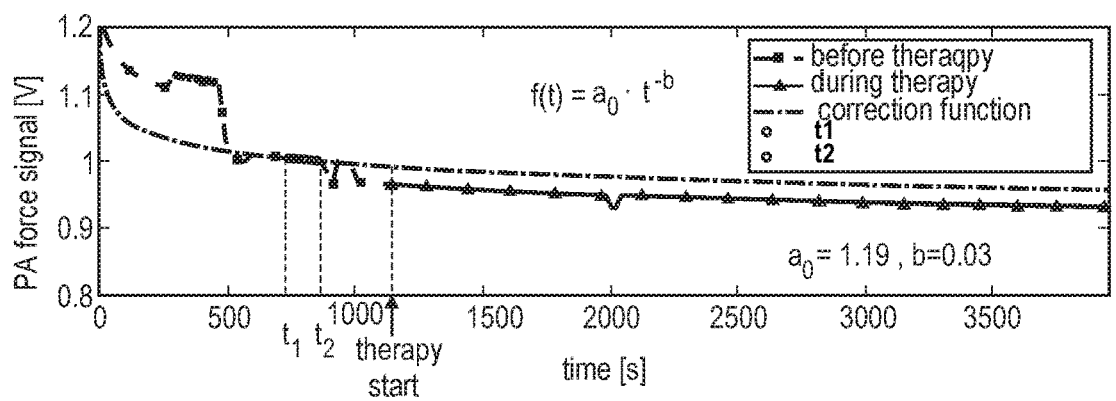
FIG. 5 shows a diagram showing the course of the drift signal at a constant internal tube pressure and the correction function representing the drift behavior of the tube.

In FIG. 5, the force signal is shown as a voltage with the unit volt [V] as a function of time t in seconds [s]. In the time range from 0 s to approx. 1200 s, during the so-called 'priming', a state exists before active use of the tube, i.e. before therapy. Before therapy, no patient is connected to the dialysis machine 6 and in this case the dialysis machine 6 is configured as described and shown in connection with FIG. 3A. In the time range starting at about 1200 s, the voltage signal during therapy is shown, also referred to as 'therapy'. During therapy, a patient is connected to the dialysis machine 6, which is then configured as described and shown in connection with FIG. 7.

In order to be able to determine the constants $a_0$ and b using this force signal, the respective signal values of the force signal f(t=t1) and f(t=t2) are determined in the fitting at two specific times t1 and t2 in the range before the therapy. In the example shown in FIG. 5, the time points t1=600 s and t2=800 s were selected. This results in the following system of equations of formulas (2) and (3), which have to be solved to obtain the constants $a_0$ and b:

$$I\ f(t=t1)=a_0 \cdot t1^{-b} \tag{2}$$

$$II\ f(t=t2)=a_0 \cdot t2^{-b} \tag{3}$$

From equation I, i.e. formula (2), $a_0$ can be represented as follows:

$$a_0 = f(t=1) \cdot t1^b \tag{4}$$

Substituting $a_0$ in the form, shown in formula (4), into formula (3) gives b in the form shown in formula (5), in which it now depends only on the known times t1, t2 and the corresponding signal values of the force signal $f(t=t1)$ and $f(t=t2)$ and can thus be calculated:

$$b = ln(f(t=t2)) - ln(f(t=t1))/(ln(t1) - ln(t2)) \tag{5}$$

After determining the value of b, this value can be inserted into formula (4), so that the value of the constant $a_0$ is obtained, and equation (1) represents the viscoelastic behavior of the tube used. With the times t1 and t2 selected above and the voltage values applicable in this experiment, the value of $a_0$ is 1.19 and the value of b is 0.03.

Step a) is shown here as an example for the PA pressure sensor and is performed analogously for the PBE pressure sensor.

Step b)

Next, the measured force signal is to be corrected and to be converted into a pressure signal using the appropriate pressure reference signal. This is done in a phase before the therapy and when the internal tube pressure changes, for example when it drops, or via a second constant pressure level with a different pressure compared to the first level. The internal tube pressure drops, for example, when the tube is disconnected from the substitute ports SP1, SP2 in preparation for therapy. A second pressure level can be set by a different pumping ratio of blood pump and flow pump. Step b) is carried out as an example for the first pressure sensor PA.

First, the drift signal f(t) with the calculated values for $a_0$ and b (value of f(t) obtained from equation (1)) is subtracted from the force signal $P_{S\_gem}$ measured with the first pressure sensor PA, which is output as a voltage value (in V). Thus, the corrected force signal $P_{S\_Korr}$ follows the following equation (formula (6)):

$$P_{S\_Korr} = P_{S\_gem} - f(t) \tag{6}$$

Figure 6:
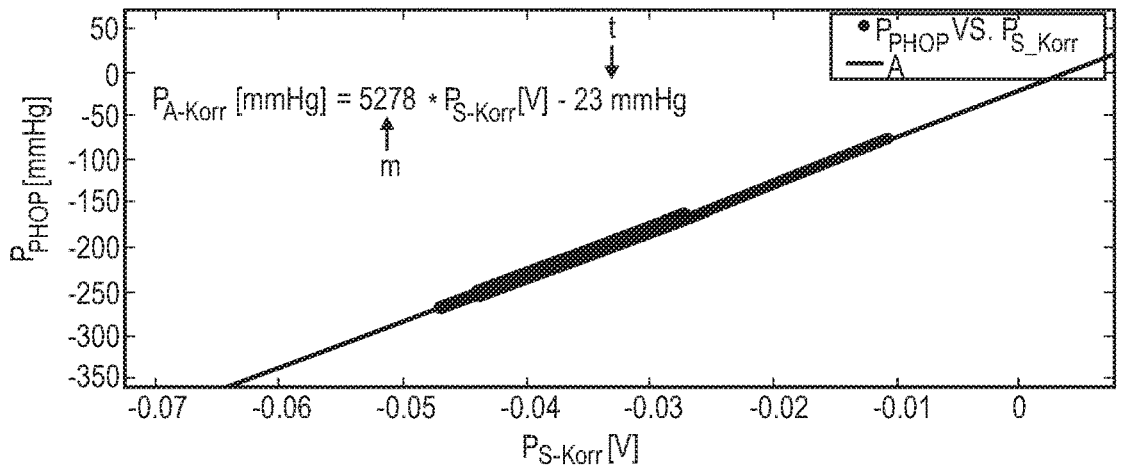
FIG. 6 shows a diagram showing graphically the determination of the pressure signal from the drift signal/force signal.

Then, using the first pressure reference sensor PHOP, pressure reference values $P_{PHOP}$ are acquired in the unit mmHg and are plotted over the associated voltage value $P_{S\_Korr}$ in [V] in a diagram, which is shown as an example in FIG. 6.

In the diagram in FIG. 6, the measured pressure reference values $P_{PHOP}$ on the y-axis are plotted as points above the calculated voltage values $P_{S\_korr}$ on the x-axis, and a linear progression/course is shown for these points. Matching this, a straight line A is determined mathematically, which runs best through these points and thus represents the relationship between voltage values $P_{S\_korr}$ and the pressure correction values $P_{A\_Korr}$ calculated from them. This relationship can be stated mathematically as follows in the form of formula (7):

$$P_{A\_Korr} = m \cdot P_{S\_korr} + t \tag{7}$$

Here, m is the slope of the line, which is also called the scaling value, and t is the pressure reference value at which the line intersects the y-axis and which is also called the offset value. In the example shown, the scaling value is 5278 mmHg/V and the offset value is 23 mmHg.

This means that the corrected and thus correct pressure signal $P_{A\_korr}$ of the first clamping device, i.e. of the first pressure sensor PA, is known before therapy and step b) is completed.

Step b) for the PBE pressure sensor is analogous to the procedure shown here for the PA pressure sensor, but here the PV pressure reference sensor is used as reference instead of the PHOP pressure reference sensor.

Since, for example, the internal tube pressure values and/or the internal tube temperatures may change from a state before therapy to a state during therapy, it is recommended that the correction for the measured force signal of the first and/or second pressure sensor is performed repeatedly during therapy.

Step c)

Figure 7:
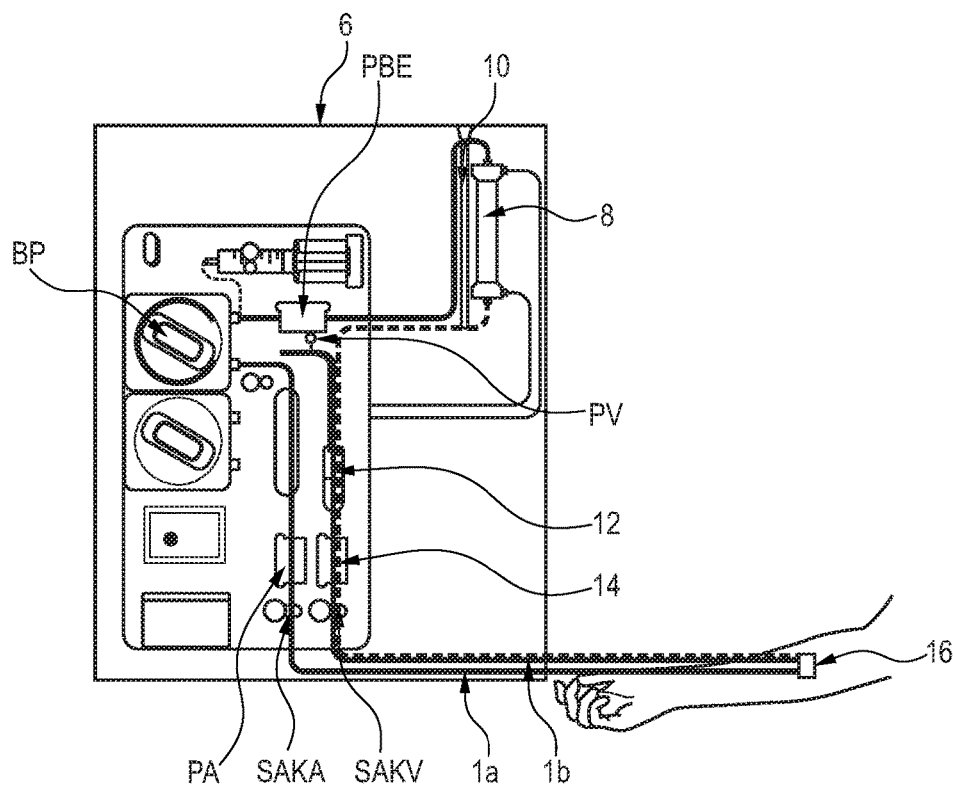
FIG. 7 shows the front of a dialysis machine in active use of the tube with a patient connected to the machine.

During therapy, the setup shown in FIG. 2A changes as shown in FIG. 7. In FIG. 7, it can be seen that the arterial and venous tube portions 1a and 1b are connected to the patient. In this case, the patient's heart replaces the dialysate inflow and outflow pumps. An (arm) artery, which is connected to the arterial tube portion 1a, and an (arm) vein of the patient, which is connected to the venous tube portion 1b, are connected to each other via an artificial connection 16, in particular via a patient shunt. As a result, the same blood pressure and the same blood flow values are present in the vein and artery (can also be referred to as blood vessels in general terms) of the patient. By setting a bypass on the dialyzer, the same blood pressures and the same blood flow values are also present in the arterial and venous tube portion 1a, 1b and thus in the entire system consisting of tube and patient veins. For experiments, it is conceivable to simulate an experimental patient circuit which has a water pump, a heated water bath and a counterpressure valve.

The principle for calibration and referencing is for step c) equal/identical as for step b). Once again, the measured force signal of the pressure sensor is corrected by the correction signal found in step a), and the corrected pressure signal can be calculated from the relationship between the corrected pressure signal and the corrected force signal known from step b) (cf. formula (6) with the scaling value and offset value determined in step b)).

Step c) may be performed for the first and second PA, PBE pressure sensors. However, here the conventional PV pressure reference sensor serves as the pressure reference sensor for both the PBE pressure sensor and the PA pressure sensor to allow simultaneous referencing of the PA pressure signal and the PBE pressure signal.

To simplify matters, it is possible to reference only the pressure signal of the second pressure sensor PBE using the pressure reference sensor PV by switching the dialyzer flow to the bypass. Due to the production-related identical properties of the tube at the position of the PA clamping device and at the position of the PBE clamping device, the correction function found for the PBE pressure signal can be applied to the PA pressure signal, even if this method is not as precise as determining a correction function for the PA pressure signal and the PBE pressure signal, respectively.

Result of the Method According to the Invention

After filtering and scaling the corrected pressure signal, this signal can be compared with the corresponding, directly measured pressure reference signal. This comparison is shown in FIG. 8 as an example for the corrected pressure signal $P_{A\_korr}$ and the corresponding pressure reference signal $P_{PHOP}$.

Figure 8:
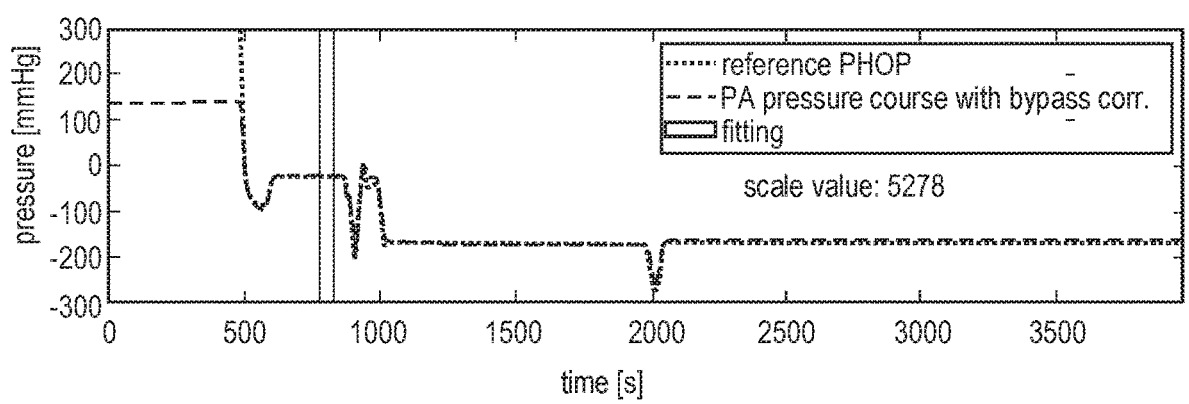
FIG. 8 shows a diagram showing an example of the pressure course at a first pressure sensor with time when the method is performed.

The diagram in FIG. 8 shows that the course of the calculated pressure correction signal $P_{A\_Korr}$ and the course of the directly measured pressure reference signal $P_{PHOP}$ are congruent. This means that the mathematical correction function from (1) together with the calculated values for $a_0$ and b can eliminate the drift course, but this only works if the internal tube pressure and the internal tube temperature are constant. If, for example, the internal tube pressure varies when the second voltage value f(t2) is measured, the correction function is not suitable for describing the course of the drift signal.

Referenceability

Figure 9:
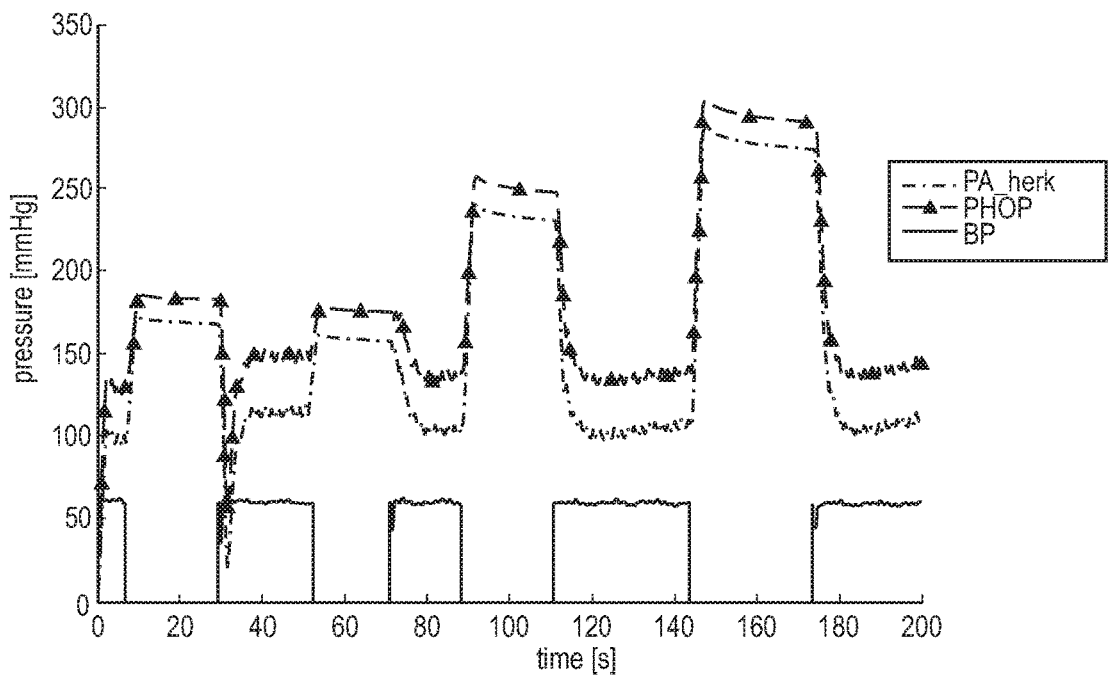
FIG. 9 shows a diagram showing the pressure courses of a conventional pressure sensor, of a first pressure reference sensor and of a first pump.
Figure 10A:
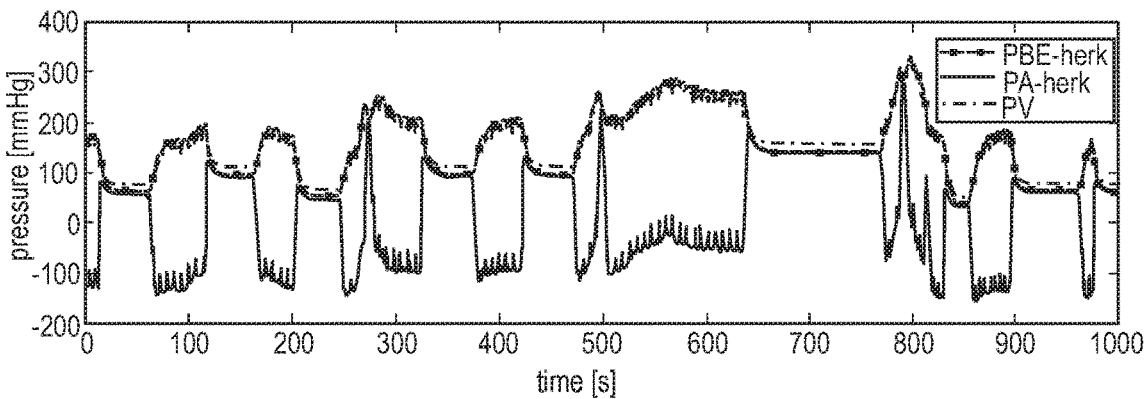
FIG. 10A shows a diagram showing the pressure courses of two conventional pressure sensors and of a second pressure reference sensor recorded simultaneously with the course curves of FIG. 10A.

In the following, FIG. 9 and FIG. 10A show the pressure courses of the conventionally used pressure sensors for measuring the arterial pressure $P_A$ and the dialyzer inlet pressure $P_{PBE}$ in comparison with the pressure course of the corresponding pressure reference sensors PHOP and PV, respectively.

In FIG. 9, the pressure course of a conventional first pressure sensor PA_herk for measuring arterial pressure is compared with the pressure course of the first pressure reference sensor PHOP before therapy. The pressure courses in mmHg are shown in the course with time t in s. Furthermore, the pressure course of the blood pump BP is shown, which repeatedly shows a pressure of 0. The blood pump BP is repeatedly stopped to generate constant pressure values of the PA_herk sensor and of the PHOP sensor.

It can be seen that the curves of the two pressure signals of the PA_herk pressure sensor and of the PHOP pressure reference sensor are similar and run parallel to each other, here with a parallel shift of the curves/a pressure difference of approx. 20 mmHg. The difference between the two pressure signal curves is due to the height differences of the first pressure sensor PA_herk and the first pressure reference sensor PHOP. In this configuration example, the first pressure reference sensor PHOP is mounted higher than the first pressure sensor PA (see FIG. 2A).

Although the pressure difference between the conventional pressure sensor and the pressure reference sensor has to be taken into account, the comparison in FIG. 9 shows that the pressure reference sensor is suitable as a reference sensor for arterial pressure.

Figure 10B:
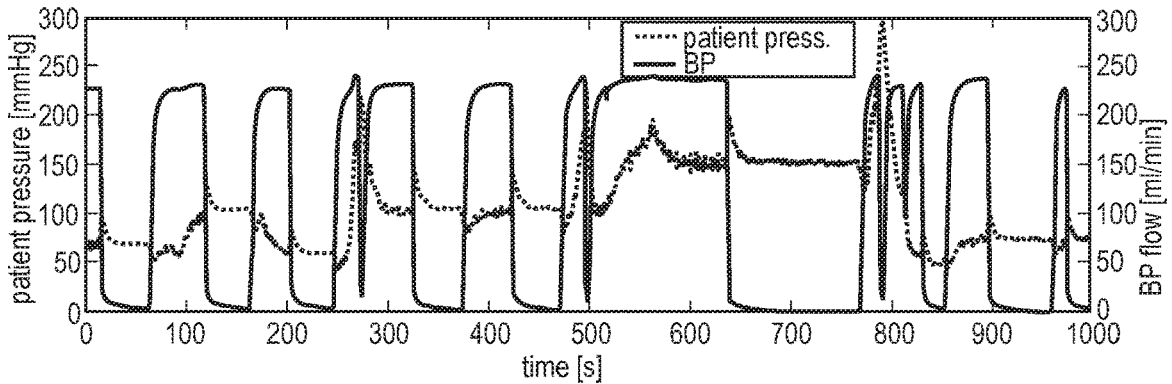
FIG. 10B shows a diagram showing the time course of a (simulated) blood flow rate of a patient and a patient blood pressure.

FIG. 10A shows the pressure courses of the first conventional pressure sensor PA_herk for measuring the arterial pressure and of a second conventional pressure sensor PBE_herk for measuring the dialyzer inlet pressure in comparison with the pressure course of the second pressure reference sensor PV in mmHg with time tin s during therapy. FIG. 10B shows a diagram depicting the time courses of the blood pump flow in ml/min and of the simulated patient pressure in mmHg, which were recorded simultaneously with the pressure values from FIG. 10A.

In the ranges in which the blood pump flow is 0, i.e. at the times when the blood pump is stopped, the pressure signals of the sensors PA_herk, PBE_herk and PV match each other and are constant. In these constant pressure ranges, the pressure courses of the two pressure sensors PA_herk and PBE_herk are essentially congruent and there is a pressure difference to the pressure course of the pressure reference sensor PV, which in this case is about 20 mmHg and can be explained by the height difference between the pressure sensors PA_herk, PBE_herk and the pressure reference sensor PV.

Again, although the pressure difference between the conventional pressure sensor and the pressure reference sensor needs to be considered, the comparison in FIG. 9 shows that the second pressure reference sensor is suitable as a reference sensor for arterial pressure and for dialysate inlet pressure during therapy.

Temperature Drift

So far, the above description has assumed a constant internal tube pressure and a constant internal tube temperature. However, between step b) and step c), i.e. between the phase before therapy and the phase during therapy, there may be temperature differences in the filled tube which can lead to linear deviations between the reference sensor value and the pressure sensor value.

Figure 11A:
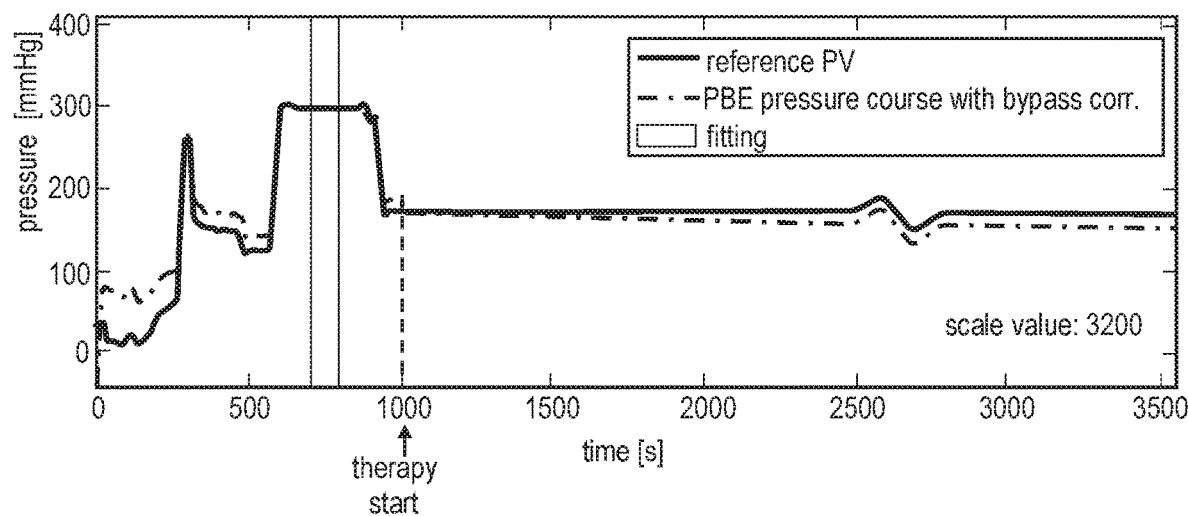
FIG. 11A shows a diagram showing a deviation between a calculated pressure signal and a reference signal due to a temperature drift.
Figure 11B:
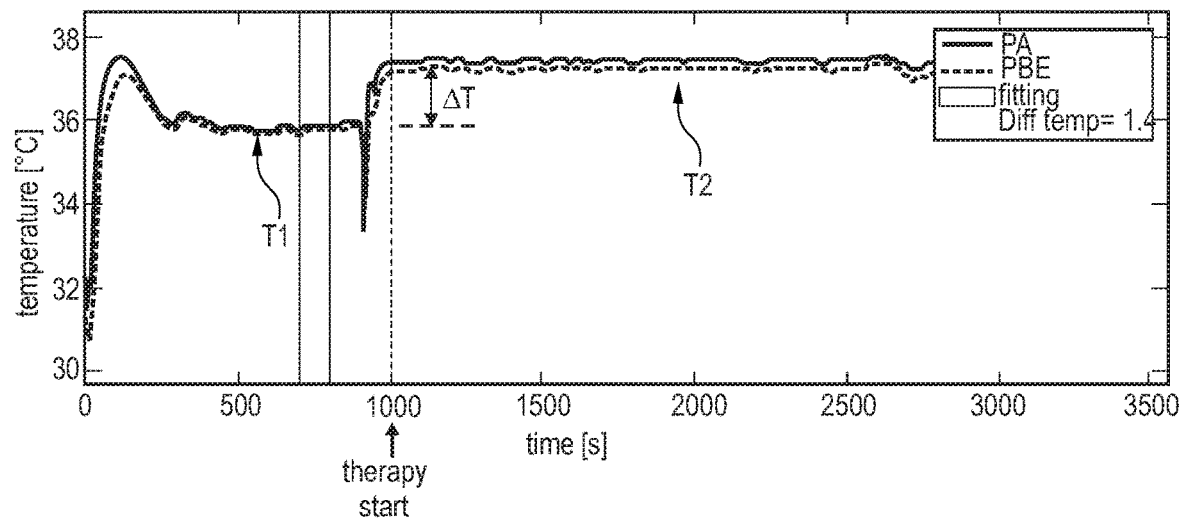
FIG. 11B shows a diagram related to the diagram in FIG. 11A showing the temperature course of a fluid in the tube at the first and second pressure sensors.

Such a deviation is exemplarily shown for the PBE pressure sensor and the PV pressure reference sensor in the diagram of FIG. 11A. FIG. 11B shows the corresponding temperature course at the measuring points of the PBE pressure sensor and the PV pressure reference sensor. In order to be able to determine the temperature at these two measuring points, it is necessary to integrate a temperature sensor into the PBE clamping device and/or into the PA clamping device. Here, calibration before therapy (up to approx. 900 s) takes place at T1, for example at 35.8° C., while calibration during therapy takes place at T2, for example at 37.2° C. Due to the temperature difference $\Delta T$ (=T2−T1) before and during therapy, which is here 1.4° C., the calculated PBE pressure signal shown in FIG. 11B does not follow the PV reference signal during therapy, but deviates linearly from it. Investigations have shown that the deviation between pressure signal and reference signal is linearly proportional to the temperature deviation before and during therapy. The pressure signal can be corrected using an empirically determined correction function.

Figure 12A:
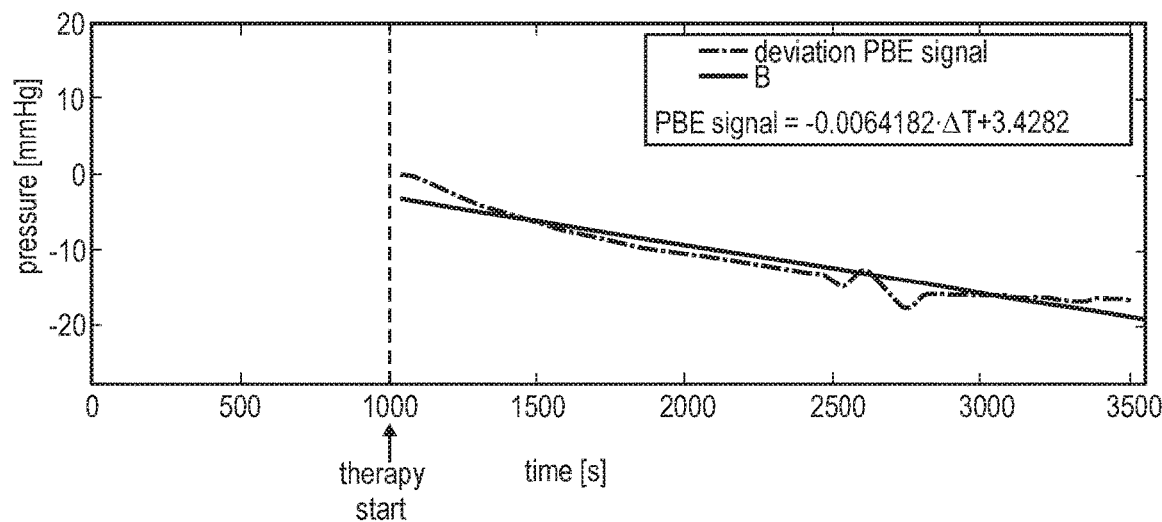
FIG. 12A shows a diagram showing the deviation of the pressure signal of the second pressure reference sensor from the corresponding pressure reference signal and showing a linear correction signal.

FIG. 12A shows the pressure deviation between pressure signal and reference signal and a straight line B over time tin s found for it. In the example, the straight line equation has the following form, which is shown in formula (8):

$$PBE_{Signal} = -0.0064182 \cdot \Delta T + 3.4282 \qquad (8)$$

Figure 12B:
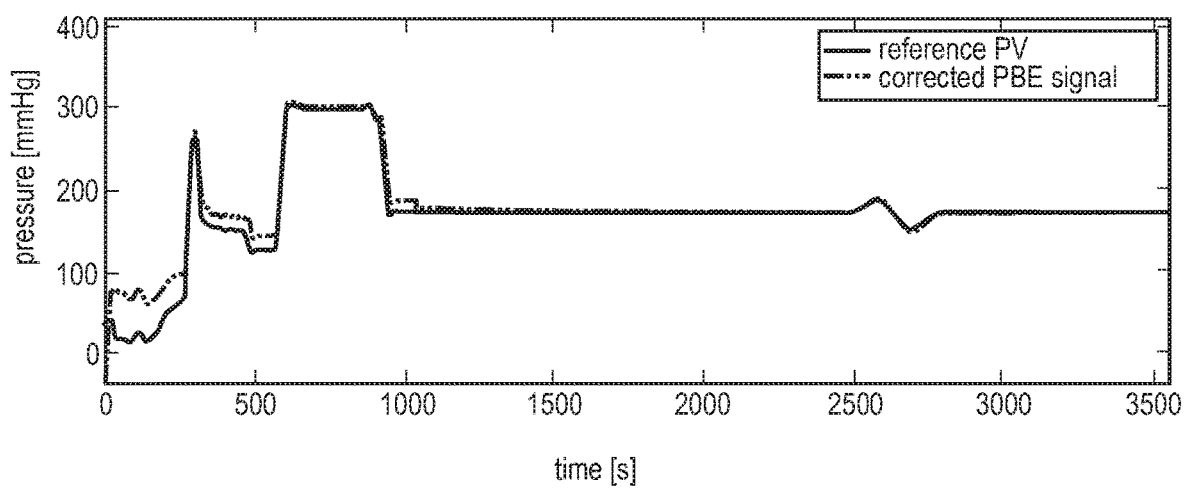
FIG. 12B shows a diagram related to the diagram of FIG. 12A showing the courses of the pressure signal corrected with the linear correction signal and of the pressure reference signal.

FIG. 12B shows the PBE pressure signal corrected using the determined formula (8), which is now again shown to be congruent with the PV reference signal.

As an alternative to a linear relationship between the deviation between pressure signal and reference signal and the temperature deviation before and during therapy, a polynomial relationship may also exist. However, more computing power is required to calculate the corresponding formula, even though such a relationship can represent the deviation more accurately than a linear one.

Figure 13A:
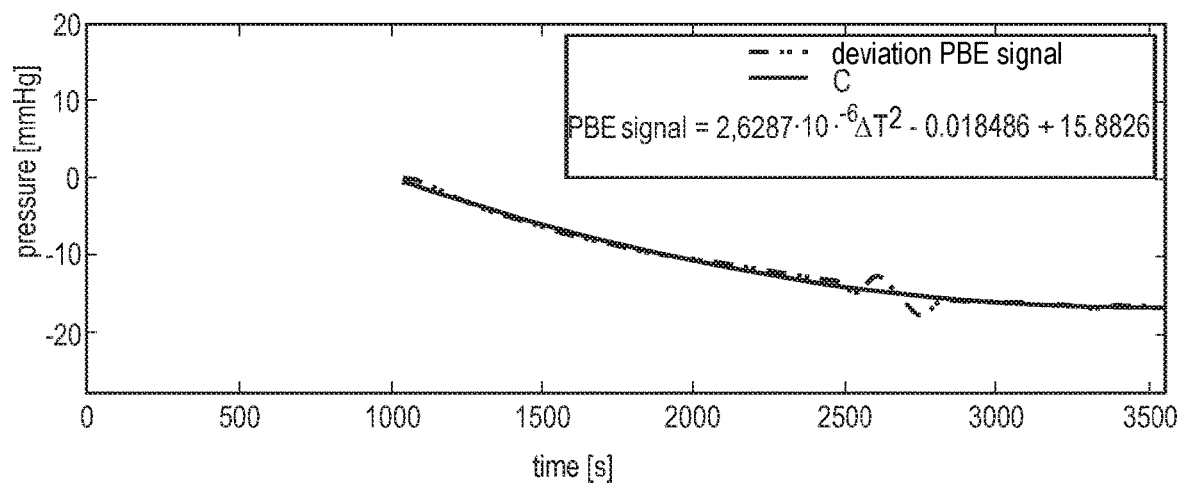
FIG. 13A shows a diagram showing the deviation of the pressure signal of the second pressure reference sensor from the corresponding pressure reference signal and a polynomized correction signal.
Figure 13B:
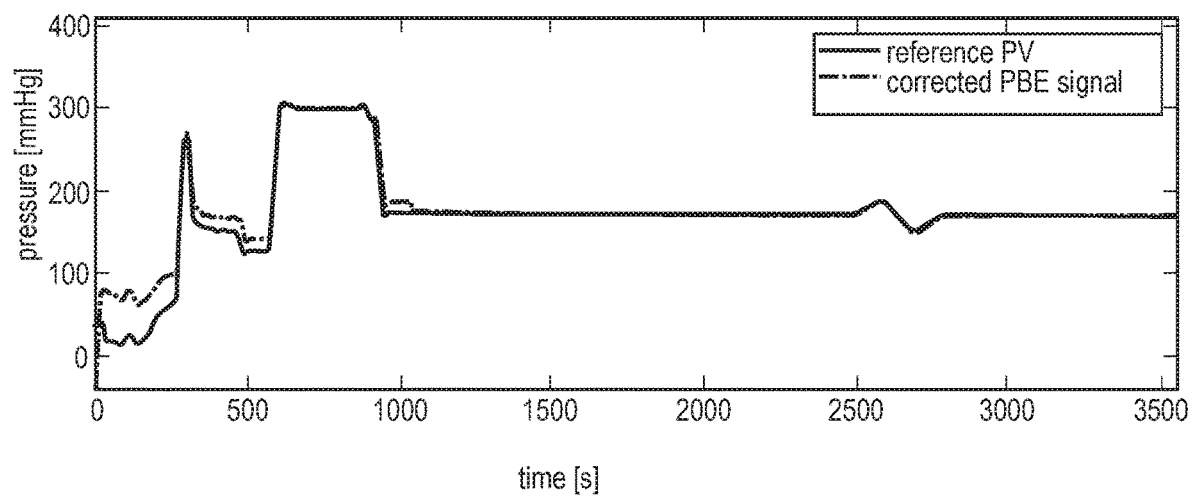
FIG. 13B shows a diagram which is related to the diagram of FIG. 13A and shows the courses of the pressure signal corrected with the polynomized correction signal and of the pressure reference signal.

FIG. 13A shows, like FIG. 12A, the pressure deviation between pressure signal and reference signal and a polynomial C calculated for it over time t in seconds. In the example, the PBE pressure signal follows the polynomial deviation shown in formula (9):

$$PBE_{Signal} = 2.687 \cdot 10^{-6} \cdot \Delta T^2 - 0.018486 + 15.8826 \qquad (9)$$

FIG. 13A shows the PBE pressure signal corrected using the determined formula (9), which is now again shown to be congruent with the PV reference signal.

Second Embodiment

The second embodiment is similar to the first embodiment, therefore only the differences to the first embodiment are elaborated below.

The reference pressure measurement of the pressure signals PBE and PA in step c) (during therapy) may also be performed using the venous tube clamp SAKV and the arterial tube clamp SAKA as an alternative to the method described in the first embodiment.

For this purpose, the dialyzer flow is switched into the bypass, as in the first configuration example, and the tube clamps SAKV and SAKA are closed. A pressure-tight connection is created in the tube. The blood pump BP is stopped. However, due to the delay, the blood pump BP continues to rotate for a short time after the stop, so that a negative pressure builds up in the arterial tube portion and a positive pressure builds up in the venous tube portion, which have the same pressure ratio to each other over time. The PBE pressure signal is calibrated using the PV pressure reference sensor. The PA pressure signal can also be calibrated using the PV pressure reference sensor.

Since the patient is cut off from the extracorporeal circuit due to the closed tube clamps SAKV and SAKA, this alternative version can be performed in step c) independently of the patient. However, in this case, the blood no longer circulates in the extracorporeal circuit, so that the blood can clot in the circulation and the temperature may drop. However, the coagulation of the blood and its temperature drop depend on the duration of the blood pump stop, which should therefore be as short as possible.

The invention claimed is:

1. A method for calibrating an output of a first sensor configured to determine a pressure of a liquid present inside a dialyzer tube at a first location in an extracorporeal circuit based on a first force signal generated by the first sensor, wherein the first sensor abuts directly on the dialyzer tube and the first sensor is integrated into or inserted into a first clamping device, the method comprising:
    a) clamping the dialyzer tube within the first clamping device;
    b) measuring a first reference signal generated by a first reference sensor before connecting the dialyzer tube to a patient, at a constant internal tube pressure and at a constant internal tube temperature,
    c) performing a regression analysis on the first reference signal to generate a prediction of at least one tube parameter-independent correction function for finding a correction signal for correcting a drift signal in the first force signal;
    d) performing a first calibration of the output of the first sensor by applying the correction signal to the output of the first sensor;
    e) measuring a second reference signal generated by a second reference sensor when the dialyzer tube is connected to the patient; and
    f) performing a second calibration of the output of the first sensor based on the second reference signal.

2. The method for calibrating according to claim 1, wherein a second sensor is integrated into a second clamping device and the method further comprises:
    calibrating an output of the second sensor according to steps a) through f) of claim 1.

3. The method for calibrating according to claim 2, wherein the dialyzer tube comprises an arterial portion and a venous portion, the first the first reference sensor are arranged at the arterial portion, and the second reference sensor is arranged at the venous portion, wherein the second reference sensor is not integrated into a clamping device and does not generate a drift signal.

4. The method for calibrating according to claim 2, wherein the first reference sensor has a higher respective measurement accuracy than the first sensor, and the second reference sensor has a higher respective measurement accuracy than the second sensor.

5. The method for calibrating according to claim 2, wherein the dialyzer tube comprises an arterial portion and a venous portion, the first sensor is arranged at the arterial portion, the second sensor is arranged at the venous portion, and wherein during calibration of the output of the first sensor and calibration of the output of the second sensor a first internal tube pressure in the arterial portion of the dialyzer tube is matched, via a bypass circuit in the arterial portion of the dialyzer tube, with a second internal tube pressure in the venous portion of the dialyzer tube.

6. The method for calibrating according to claim 2, wherein:
    the first sensor is arranged at an inlet opening of a pump, and
    the second sensor is arranged at an outlet opening of the pump.

7. The method for calibrating according to claim 1, wherein the constant internal tube pressure is obtained before the dialyzer tube is connected to the patient by adjusting a pumping ratio between a first pump and a second pump.

8. The method for calibrating according to claim 1, wherein the drift signal is or corresponds to a reset force of the dialyzer tube in a clamped state.

9. The method for calibrating according to claim 1, wherein the output of the is converted into a pressure signal by the first reference signal via a linear recursion.

10. A device comprising:
    an extracorporeal circuit,
    a first sensor integrated into a clamping device that is clamped to a fluid-filled dialyzer tube having an arterial portion and a venous portion, wherein the first sensor is configured to generate a force signal representative of an internal tube pressure in the fluid-filled dialyzer tube,
    a first reference sensor configured to generate a reference signal, wherein the first reference sensor is not integrated into any clamping device,
    at least a first pump and a second pump, and
    a computer configured to calibrate an output of the first sensor based on the reference signal by:
    a) measuring a first reference signal generated by the first reference sensor before connecting the fluid-filled dialyzer tube to a patient, at a constant internal tube pressure and at a constant internal tube temperature,
    b) performing a regression analysis on the first reference signal to generate a prediction of at least one tube parameter-independent correction function for finding a correction signal for correcting a drift signal in the force signal;
    c) performing a first calibration of the output of the first sensor by applying the correction signal to the output of the first sensor;
    d) measuring a second reference signal generated by a second reference sensor when the fluid-filled dialyzer tube is connected to the patient; and
    e) performing a second calibration of the output of the first sensor based on the second reference signal.

* * * * *